United States Patent

Zhang et al.

[11] Patent Number: 6,005,125
[45] Date of Patent: Dec. 21, 1999

[54] UNIVERSAL ALLYL LINKER FOR SOLID-PHASE NUCLEIC ACID SYNTHESIS

[75] Inventors: Xiaohu Zhang, Piscataway; Roger A. Jones, Martinsville, both of N.J.

[73] Assignee: Rutgers the State University of New Jersey, N.J.

[21] Appl. No.: 08/852,110

[22] Filed: May 6, 1997

Related U.S. Application Data

[60] Provisional application No. 60/016,948, May 6, 1996.

[51] Int. Cl.$^6$ .................................................... C07C 59/00
[52] U.S. Cl. ........................... 554/218; 554/213; 560/57; 560/58; 560/101; 562/468; 562/470; 564/181
[58] Field of Search .................................. 536/25.3, 23.1; 562/405, 468, 470; 560/8, 57, 58, 101, 183; 564/181; 554/35, 65, 68, 116, 124, 132, 213, 218

[56] References Cited

PUBLICATIONS

Beaucage et al, Tetrahedron, vol. 48, pp. 2223–2311, 1992.
Pon, Protocols for Oligonucleotides and Analogs,Agrawal, S.ed.;Humana Press:Totowa,NJ, vol. 20, 1993.
Umbreit et al, Journal of American Chemical Society, vol. 99, pp. 5526–5528, 1977.

*Primary Examiner*—Shailendra Kumar
*Assistant Examiner*—Sreeni Padmanabhan
*Attorney, Agent, or Firm*—Davidson Davidson & Kappel, LLC

[57] ABSTRACT

A universal linker for solid-phase nucleic acid synthesis that is cleaved under conditions orthogonal to those used during the synthesis and deprotection of nucleic acids such as dsDNA or RNA fragments is disclosed. The invention includes compounds of the formula:

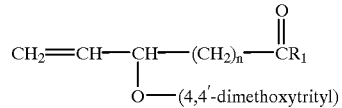

wherein $R_1$ is selected from the group consisting of OH, $OR_2$ and an amino functionalized support and n is an integer ranging from about 1 to about 1000 or more preferably from about 1 to about 100 or greater and $R_2$ is an alkyl ($C_{1-20}$) or greater.

5 Claims, 4 Drawing Sheets

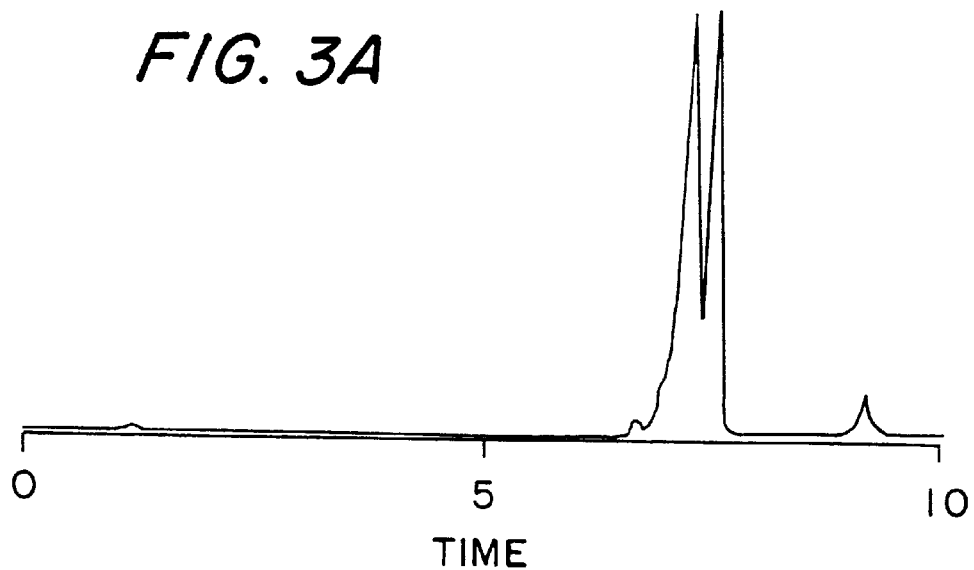
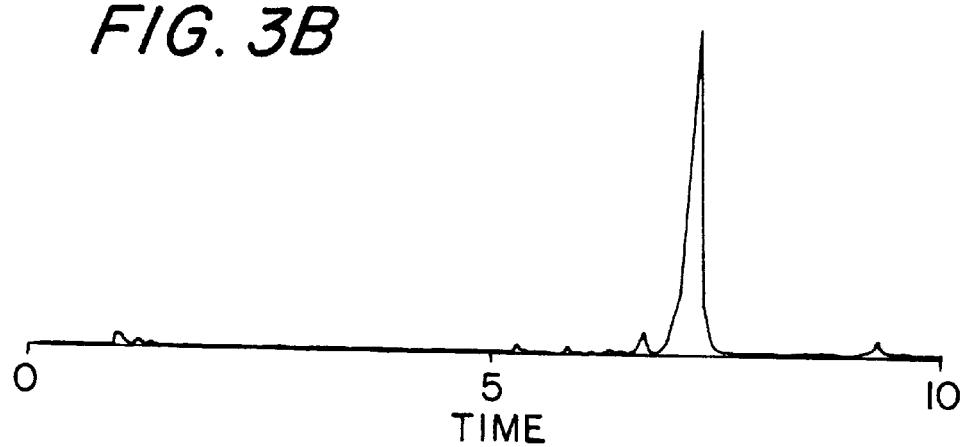

UNIVERSAL ALLYL LINKER FOR SOLID-PHASE NUCLEIC ACID SYNTHESIS

This application claims the benefit of Provisional U.S. patent application No. 60/016,948 filed May 6, 1996.

This invention was made in part with support from the National Institutes of Health, Grant No. GM 48802, and the United States Government may have certain rights in the invention.

The present invention is related to a universal linker for solid-phase nucleic acid synthesis that is cleaved under conditions orthogonal to those used during the synthesis and deprotection of nucleic acids such as dsDNA or RNA fragments.

Solid-phase synthesis of DNA and RNA fragments most commonly employs a succinate linkage between the 3'-terminal nucleoside and an amino functionalized support, although other linkages have been proposed for specific, generally limited, uses (Pon, R. T. in *Protocols for Oligonucleotides and Analogs*, Agrawal, S. ed.; Humana Press: Totowa, N.J., 1993; Vol. 20; Beaucage, S. L.; Iyer, R. P. *Tetrahedron* 1992, 48, 2223–2311). A particular deficiency of the succinate and other non-universal linkages is the need for preparation of specially derivatized 3' monomers, and an additional set of reactions, to load the 3' monomer onto the support. Moreover, the lability of the succinate linkage limits the types of post-synthetic manipulations that can be carried out on the support-bound nucleic acid fragment. RNA synthesis, for example, requires deprotection of the 2'-O-tert-butyldimethylsilyl (BDMS) group after deprotection of the amino groups. With a succinate linkage amino deprotection cleaves the RNA from the support. Once the RNA has been cleaved from the support it becomes more difficult to achieve the anhydrous conditions necessary for reaction with tetra-n-butylammonium fluoride (TBAF), and removal of the excess TBAF is time-consuming (Sproat, B.; Colonna, F.; Mullah, B.; Tsou, D.; Andrus, A.; Hampel, A.; Vinayak, R. *Nucleosides & Nucleotides* 1995, 14, 255–273).

An alternative linker system that has been used instead of TBAF is triethylamine tris(hydrogen fluoride) (Gaspaeutto, D.; Livache, T.; Bazin, H.; Duplaa, A. M.; Guy, A.; Khorlin, A.; Molko, D.; Roget, A.; Téoule, R. *Nucleic Acids Res.* 1992, 20, 5159–5166) which is less sensitive to water (Westman, E.; Stromberg, R. *Nucleic Acids Res.* 1994, 22, 2430–2431), and more easily removed than is TBAF (Sproat et al., Id.). However, triethylamine tris(hydrogen fluoride) may not be compatible with trityl-on purification of the RNA fragment. The Pd(0) mediated reactions of allyl groups were introduced by Hayakawa and Noyori for phosphate protection in 1985 (Hayakawa, Y.; Uchiyama, M.; Kato, H.; Noyori, R. *Tetrahedron Lett.* 1985, 26, 6505–6508), who then extended this methodology to the allyloxycarbonyl group for hydroxyl and amino protection (Hayakawa, Y.; Kato, H.; Uchiyama, M.; Kajino, H.; Noyori, R. *J. Org. Chem* 1986, 51, 2400–2402 and Hayakawa, Y.; Wakabayashi, S.; Kato, H.; Noyori, R. *J. Am. Chem. Soc.* 1990, 112, 1691–1696). The use of the allyl groups were then applied solid phase peptide synthesis, where several different allylic linkers containing internal double bonds were reported (Kunz, H.; Dombo, B. *Angew. Chem. Int. Ed. Engl.* 1988, 27, 711–713; Blankemeyre-Menge, B.; Frank, R. *Tetrahedron Lett.* 1988, 46, 5871–5874; Guibé, F.; Dangles, O.; Balavoine, G. *Tetrahedron Lett.* 1989, 30, 2641–2644 and Umbreit, M. A.; Sharpless, K. B. *J. Am. Chem. Soc.* 1977, 99, 5526–5528).

Therefore, there remains a need in the art for improved linkers for solid state nucleic acid synthesis avoiding the disadvantages previously known linkers. There also remains a need for a linker for solid phase nucleic acid synthesis that would be universal, and would be cleaved under completely different conditions from other linkers used in nucleic acid synthesis and that would have a highly reactive terminal double bond.

OBJECTS OF THE INVENTION

Accordingly, in order to overcome these aforementioned problems and disadvantages in the art, it is therefore an object of the present invention to provide an improved linker, for conducting solid phase nucleic acid synthesis and other suitable reactions, that would be a universal linker, and that would be cleaved under completely different conditions compared to other reactions used in nucleic acid synthesis and that provides a terminal double bond that is more reactive than terminal double bonds of previous linkers.

It is a further object of the present invention to provide methods of preparing allyl linkers for conducting solid-phase nucleic acid synthesis.

It is yet a further object of the present invention to provide improved methods of conducting solid phase nucleic acid synthesis and in particular for conducting solid phase synthesis of deoxyribonucleic acid ("DNA") and ribonucleic acid ("RNA").

It is yet another object of the present invention to provide improved solid state supports with linkers thereon for use in conducting solid phase synthesis of nucleic acids, such as DNA and RNA.

SUMMARY OF THE INVENTION

In accordance with the above objects and others which will be apparent from the further reading of the specification and of the appended claims, the present invention is related to the surprising discovery that dimethoxytrityl derivatives of alkenoic acids provide improved linkers for solid phase nucleic acid synthesis. In particular, compounds of the formula

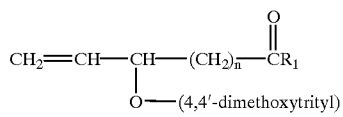

wherein $R_1$ is selected from the group consisting of OH, $OR_2$ and an amino functionalized support and n is an integer ranging from about 0 to about 1000 or more preferably from about 0 to about 100 or greater and $R_2$ is an alkyl ($C_{1-20}$) or greater. In a particular embodiment, n is, for example 7 and $R_2$ is OH.

The invention also provides for methods for preparing the linkers according to the invention by a process of selenium dioxide oxidation of a terminal alkenoic acid or its alkyl ester, e.g., methyl ester, to form the corresponding allylic alkoxy derivatives which are in turn tritylated.

The invention further provides for methods for preparing an amino or hydroxy functionalized support having the tritylated linker attached thereto. Thus, improved supports for solid phase nucleic acid synthesis can be prepared and are provided by the present invention. The improved solid phase supports of the invention are also used to provide improved methods of conducting solid phase nucleic acid synthesis according to the invention.

BRIEF DESCRIPTION OF THE DRAWINGS

FIGS. 3A and B are co-injection high pressure liquid chromatography analysis of an RNA decamer synthesized using a DMT-derivative allyl linker and an identical RNA decamer synthesized using a prior art succinate linker.

DETAILED DESCRIPTION OF THE INVENTION

Figure 1A:
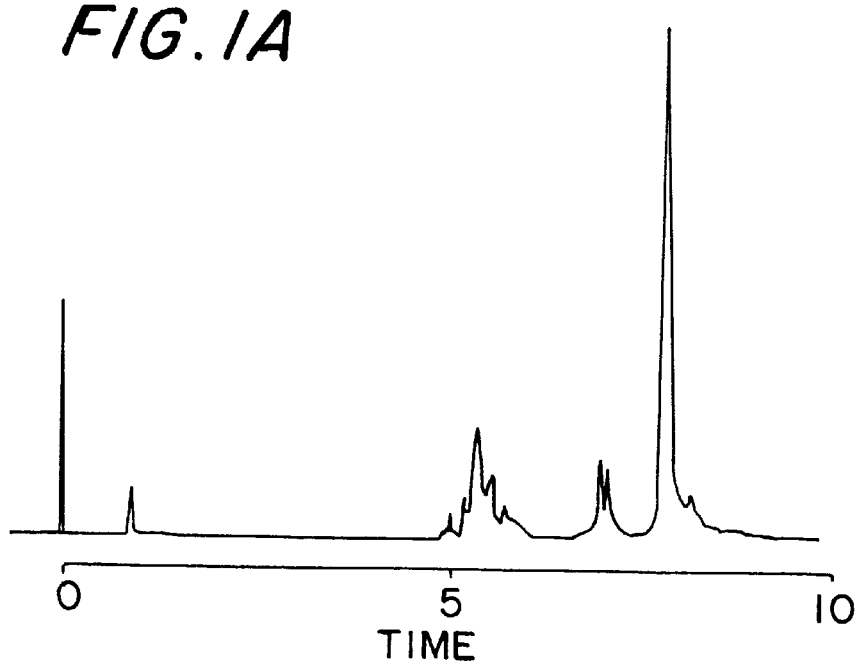
FIG. 1 is a high pressure liquid chromatography analysis of an RNA decamer synthesized using a DMT-derivative allyl linker and an identical RNA decamer synthesized using a prior art succinate linker.

Accordingly, the present invention provides an allylic linker with a more reactive terminal double bond, as well as improved supports and methods for solid phase nucleic acid synthesis. Thus, compounds of the formula

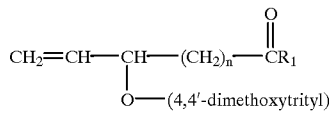

wherein $R_1$ is selected from the group consisting of OH, $OR_2$ and an amino functionalized support and n is an integer ranging from about 0 to about 1000 or more preferably from about 0 to about 100 or greater and $R_2$ is an alkyl ($C_{1-20}$) or greater. In reaction scheme 1 provided below, simply by way of example, illustrated below, the compound prepared is 9-O-(4,4'-dimethoxytrityl)-10-undecenoic wherein n is 7 and $R_2$ is OH. The preparation of the linkers according to the invention is as follows (Scheme I):

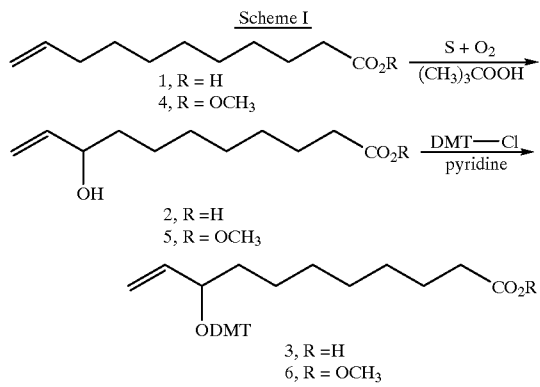

The preparation of the linker molecule, 9-O-(4,4'-dimethoxytrityl)-10-undecenoic (3), shown in Scheme 1, is a straightforward two step synthesis. The key step is a selenium dioxide oxidation (Umbreit, M. A.; Sharpless, K. B. *J. Am. Chem. Soc.* 1977, 99, 5526–5528) of a terminal alkenoic acid, in this case 10-undecenoic acid (1), or its methyl ester (4), to give the corresponding allylic alkoxy derivatives (2) or (5) in about 75% yield. The ester (5) is purified by distillation, while crude (2) is used directly in the next step. Tritylation of (2) or (5) to give the DMT derivatives (3) or (6) proceeds under standard conditions using 4,4'-dimethoxytrityl chloride (DMT-Cl) in pyridine. While in principle many terminal alkenoic acids could be used in this synthesis, the low cost of 10-undecenoic acid (1) make it particularly attractive. (The Aldrich price for 1 is $10.55 for 100 mL) The allyl linker molecule (3), after purification by silica gel chromatography, then can be attached to any amino or hydroxy functionalized support by a variety of standard procedures (Pon Id). We use amino functionalized polystyrene/polyethylene glycol[14] in methylene chloride with DCC,[15] which gives loadings of about 170 μmole/g, as determined by trityl assay (Scheme 2).

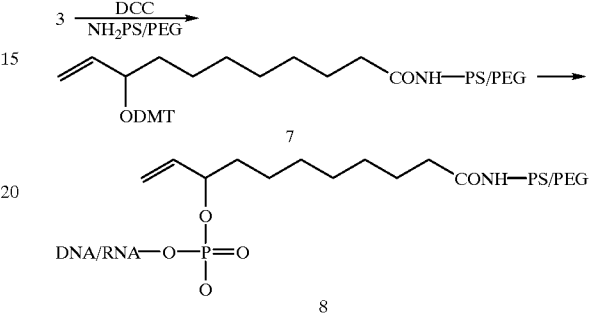

Automated DNA or RNA synthesis with support-bound DMT derivative (3) can be carried out by any of the standard nucleic acid synthetic methods. We employ an H-phosphonate procedure, but the more common phosphoramidite procedure could be used equally well. The synthesis proceeds exactly as with succinate linked material, except that it is the 3' terminal monomer, not the penultimate monomer, that is added in the first coupling step. The only changes in the procedure are in the deprotection and cleavage steps. Treatment with aqueous ammonia will not cleave the product from the support, and at this stage the product is the same regardless of the synthetic method used. The 5'-DMT can be removed, if desired, or left on for a trityl-on purification. Importantly, for RNA synthesis desilylation with TBAF or TEA·3HF can be carried out while the RNA fragment is attached to the support, and the excess reagent removed simply by washing the support-bound RNA with appropriate solvents. In addition, the ammonia treatment will cleave DNA fragments at any depurinated sites so that the 5'-DMT portion of these fragments is removed, thereby significantly simplifying the purification (Horn, T.; Urdea, M. S. *Nucleic Acids Res.* 1988, 16, 11559–11571).

After the desired deprotection steps have been completed and the reagents and cleavage products washed from the support-bound nucleic acid fragment, cleavage of the product from the support is effected using tetrakis (triphenylphosphine)palladium and n-butylammonium formate at 60° C. for 2 h. These are standard conditions for cleavage of allyl groups which have been modified by including 20% pyridine in the solvent mixture, along with the standard THF. This treatment cleaves the oligomer from the support as the 3'-phosphate. Because the nucleic acid fragment is not soluble in this THF/pyridine mixture, the reagents used in the cleavage step can be removed simply by washing the now support-adsorbed, rather than support-bound, nucleic acid fragment. The product is then dissolved and eluted from the support with 0.1 M triethylammonium acetate (TEAA) buffer. This solution can be directly applied to a reversed-phase HPLC column for purification. Small (mg) amounts of dimethyldithio carbamate in the TEAA help to remove any remaining Pd (Minczewski, J.;

Chwastowska, J.; Dybczynski, R. *Separation and Preconcentration Methods in Inorganic Trace Analysis*; John Wiley & Sons: New York, 1982, pp 207–209.

Figure 1B:
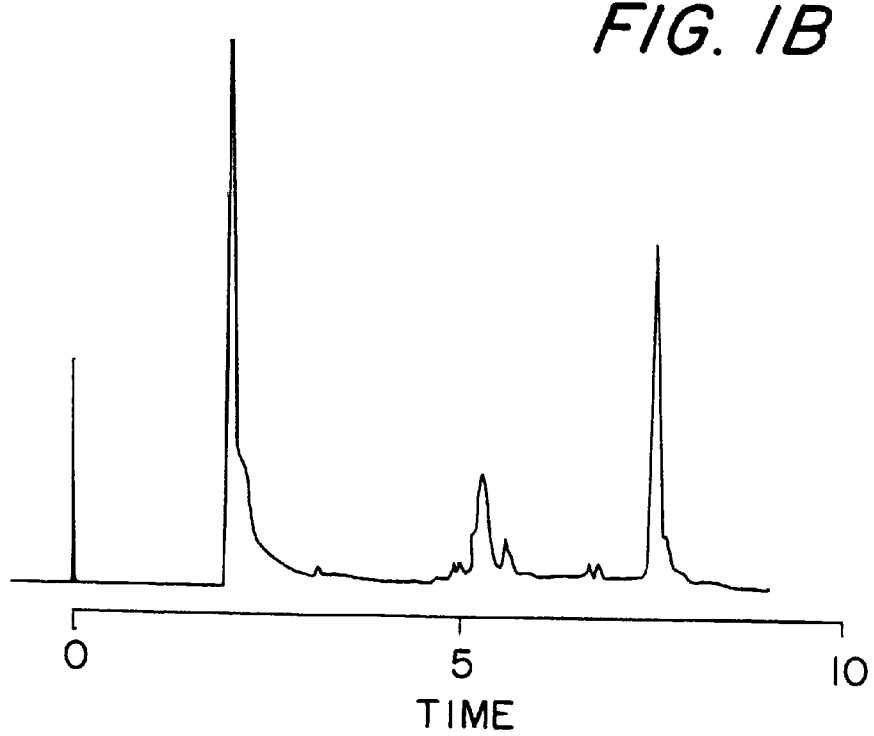
Figure 2:
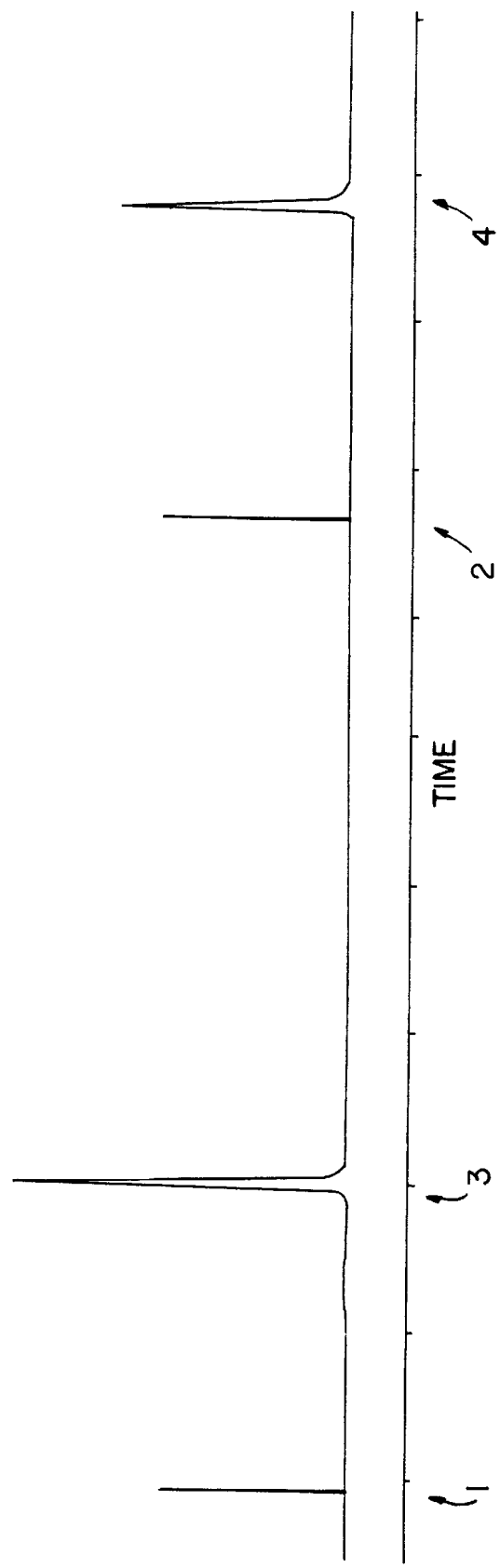
FIG. 2 is a reversed phase high pressure liquid chromatography analysis of an RNA decamer synthesized using a DMT-derivative allyl linker and an identical RNA decamer synthesized using a prior art succinate linker.
Figure 4:
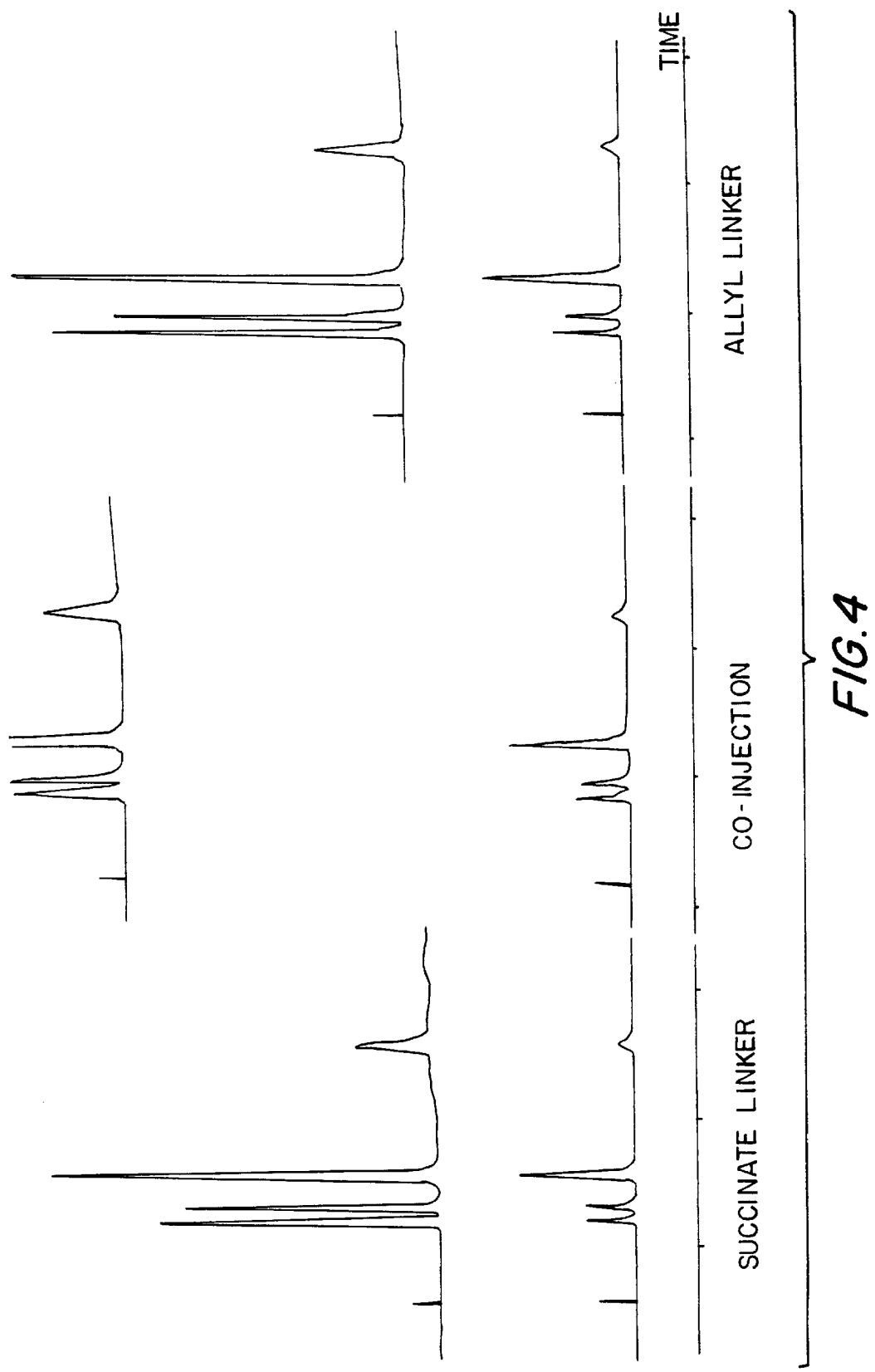
FIG. 4 is a high pressure liquid chromatography analysis of the enzymatic degradation of an RNA decamer sytnesized using a DMT-derivative allyl linker and an identical RNA decamer synthesized using a prior art succinate linker.

To illustrate use of this linker in RNA synthesis, we compared two RNA decamers, one synthesized using the DMT-derivative allyl linker and the other synthesized using a prior art succinate linker. FIG. 1 shows analytical high pressure liquid chromatography ("HPLC") analyses of the crude product mixtures after all of the protecting groups but the 5'-DMT have been removed, and the allyl linker has been cleaved from the support. FIG. 1A shows the HPLC analysis of the RNA decamer synthesized using the DMT-derivative allyl linker and FIG. 1B shows the HPLC analysis of the identical RNA decamer synthesized using the prior art succinate linker. Each was then purified by reversed-phase ("RP-BPLC"), detritylated with 0.1 M acetic acid, purified again by RP-HPLC, desalted by RP-HPLC using ammonium bicarbonate buffer, and converted to the sodium form using a sodium ion-exchange column. Each was then homogeneous by RP-HPLC, as shown in FIG. 2. FIG. 2, which has the same time scale as FIG. 1, contains point 1, the injection point for the RNA decamer synthesized using the prior art succinate compound, and point 2, the injection point for the RNA decamer synthesized using the DMT-derivative allyl linker. Peak 3 is of the RNA synthesized using the succinate linker, and Peak 4 is of RNA synthesized using the allyl linker. The overall yields of RNA decmaer synthesized using the allyl-linker (1.6 μmole, 5.3%) and the identical RNA decamer synthesized using the prior art succinate linker (2.2 μmole, 7.4%) were similar, despite the inadvertent handling loss of a portion of the RNA synthesized using the allyl linker during the purification. The different retention of the RNA decamer synthesized using the allyl linker and the RNA decamer synthesized using the prior art succinate linker due to the 3'-phosphate on the allyl linker is evident in the co-injection shown of the RNA decamer synthesized with the allyl linker and RNA decamer synthesized with the succinate linker in FIG. 3A. If desired, the 3'-phosphate on the allyl linker can be removed conveniently by treatment with a phosphatase. In this case, treatment of the RNA decamer synthesized with the allyl linker with calf intestinal phosphatase (CIP) for 1 h completely removed the phosphate group as shown by the co-injection with the RNA decamer synthesized with the prior art succinate linker in FIG. 3B. Further, enzymatic degradation of the RNA decamer synthesized with the allyl linker and the identical RNA decamer synthesized with the prior art succinate linker using nuclease P1 and CIP gave an identical mixture of monomers in the expected ratios as shown in FIG. 4. ICPMS analysis of the RNA decamer synthesized with the allyl linker showed only traces of residual Pd ($2 \times 10^{-3}$ atoms of Pd per RNA molecule). This is nearly identical to the level reported by Hayakawa and Noyori for use of allyl protecting groups in the synthesis of a DNA fragment ($3 \times 10^{-3}$ atoms of Pd per 32-mer DNA molecule) (Hayakawa, Y.; Wakabayashi, S.; Kato, H.; Noyori, R. *J. Am. Chem. Soc.* 1990, 112, 1691–1696) and confirms that Pd contamination should not be a problem for either RNA or DNA synthesis. The results reported above demonstrate that 9-O-(4,4'-dimethoxytrityl)-10-undecenoic (3) is a universal linker for solid-phase nucleic acid synthesis, that might also find application to peptide synthesis. Further, because it is cleaved under conditions orthogonal to those used during the synthesis and deprotection of DNA or RNA fragments, it extends significantly the range of post-synthetic manipulations that can be carried out without cleavage from the support. The ability to remove the 2'-O-BDMS groups while the RNA fragment is attached to the support is a particular advantage to RNA synthesis. In addition, it should improve purification of DNA molecules by allowing removal of the 5'-DMT (n–x) fragments that result from depurination.[16] This linkage also could be used to construct affinity columns or, alternatively, it should be possible in many cases to cleave fully protected molecules from the support if so desired.

In order to exemplify the results achieved using the method of the invention the following examples are provided without any intent to limit the scope of the instant invention to the discussion therein.

EXAMPLES

9-O-(4,4'-Dimethoxytrityl)-10-undecenoic acid (3)

Method A. To a solution of 12 g of 10-undecenoic acid (1, 65 mmol) in 100 mL of dry acetone were added 7.4 mL of $(CH_3)_2SO_4$ (78 mmol), and 13.2 g (96 mmol) of $K_2CO_3$. The mixture was stirred at reflux for 24 hours, cooled to room temperature, filtered, and the filtrate concentrated. The liquid residue was distilled under reduced pressure (b.p. 89° C. at 1.5 mm Hg) to give 9.6 g (74%) of 4. $^1$H NMR ($CDCl_3$) d 5.74(m, 1H, $H_{10}$), 4.90(m, 2H, $H_{11,11'}$), 3.61(s, 3H, $OCH_3$), 2.27(t, 2H, $H_{2,2'}$), 2.00(m, 2H, $H_{9,9'}$), 1.27-1.62(m, 12H, $CH_2$'s 3–8). To a mixture of 1.1 g of $SeO_2$ (10 mmol) and 8.5 mL of t-butylhydroperoxide (5.0–6.0 M in decane) in 50 mL of $CH_2Cl_2$ stirred at room temperature for 30 min was added dropwise a solution of 4.1 g (20 mmol) of 4 in 10 mL of $CH_2Cl_2$. The reaction mixture was stirred for two days, washed with brine and concentrated. The liquid residue was distilled (135° C., 1.5 mm Hg) to give 1.0 g (23%) of 5. $^1$H NMR ($CDCl_3$) d 5.94(m, 1H, $H_{10}$), 5.24(m, 2H, $H_{11,11'}$), 4.12(m 1H, $H_9$), 3.66(s, 3H, $OCH_3$), 2.34(t, 2H, $H_{2,2'}$), 1.64-1.17(m, $CH_2$'s 3–8). To a solution of 1.5 g (7 mmol) of 5 in 25 mL of pyridine was added 3.6 g of 4,4'-dimethoxytrityl chloride (DMTCl, 10.7 mmol). The reaction mixture was stirred at room temperature overnight, filtered, the filtrate concentrated and the residue purified by normal phase HPLC to give 3.46 g (6.7 mmol, 96%) of 6 as a viscous liquid. 1H NMR($CDCl_3$) d 7.51-6.77(m, 13H, ArH's), 5.72(m, 1H, $H_{10}$), 4.83(m, 2H, $H_{11,11'}$), 3.90-3.79 (m and s, 7H, $H_9$ and Ar-$OCH_3$'s), 3.66(s, 3H, $OCH_3$), 2.31(t, 2H, $H_{2,2'}$) 1.65-1.09(m, $CH_2$'s 3–8). To a mixture of 25 mL of THF and 5 mL of water were added 3.46 g (6.7 mmol) of 6 and 1.1 g (20 mmol) of KOH. The reaction mixture was refluxed overnight, cooled and partitioned with 150 mL each of water and ethyl ether.

The aqueous layer was then extracted with a 150 mL portion of a 1:1 mixture of ethyl ether and ethyl acetate. The latter organic layer was concentrated to give 3.2 g of 3 (5.9 mmol, 88%) as a wax. $^1$H NMR($CDCl_3$), d 7.51-6.75(m, 13H, ArH's), 5.71(m, 1H, $H_{10}$), 4.83(m, 2H, $H_{11, 11'}$), 3.90-3.79(m and s, 7H, $H_9$ and Ar-$OCH_3$'s), 2.82(b, 2H, $H_{2,2'}$), 1.50-1.15(m, $CH_2$'s 3–8). IR (film) cm$^{-1}$, 3452, 2930, 2856, 1739, 1437, 1363, 1247, 1199, 1173, 992, 920.

Method B. To a mixture of 0.36 g (3.2 mmole) of $SeO_2$ and 50 mL of methylene chloride was added 6.5 mL of a 5–6 M solution of tert-butyl hydroperoxide in decane. The mixture was stirred at room temperature for 30 min and a solution of 2.0 g (11 mmole) of 10-undecenoic acid (1) in 10 mL of $CH_2Cl_2$ was added dropwise. The mixture was stirred at room temperature for 2 d, washed successively with water and brine, dried over $Na_2SO_4$, and concentrated to an oil (oil pump, 50° C.). GC/MS showed that this material contained about 25% of unreacted 1. This mixture was used in the next step without purification. To the above crude 2 dissolved in 25 mL of pyridine was added 4.5 g (13 mmole) of 4,4′-dimethoxytrityl chloride. After 16 h at room temperature the mixture was filtered, concentrated and the product purified by chromatography on silica gel using a gradient of 2% pyridine in petroleum ether to 2% pyridine, 2% methanol, and 30% ethyl acetate in petroleum ether. Concentration of the product containing fractions gave 2.4 g (4.1 mmole, 38% from 1) of 3 as the pyridinium salt. MS (+FAB) m/e, 502.3 (M+, $C_{32}H_{38}O_5$ requires 502.7), (−FAB) m/e 501.5 (M-H+, $C_{32}H_{37}O_5$ requires 501.7).

Attachment to amino-functionalized polystyrene/polyethylene glycol. To a 3 mL portion of $CH_2Cl_2$ was added 220 mg (0.38 mmole) of 3, 130 mg (0.63 mmole) of dicyclohexylcarbodiimide, and 600 mg of polystyrene/polyethylene glycol (PS/PEG).[1] The viscous mixture was shaken at room temperature for 16 h, filtered, and the support washed successively with $CH_2Cl_2$, methanol, $CH_2Cl_2$, and diethyl ether. The unreacted amino groups remaining on the support were capped using 10% acetic anhydride in a solution of 1% N-methyl imidazole in pyridine for 2 h at room temperature. The mixture was filtered, and the support washed successively with $CH_2Cl_2$, methanol, $CH_2Cl_2$, and diethyl ether. After drying under vacuum the typical loading range is 150–180 μmole/g.

Procedure for determining loading of 3 onto PS/PEG. To a 100–120 mg sample of the derivatized support was added 2–3 mL of 2.5% dichloroacetic acid (DCA). After 2 min the mixture was filtered and the support washed with three additional portions of DCA. The combined filtrates were diluted to 500 mL and the absorbance measured at 502 nm. The loading was calculated using an extinction coefficient of $9 \times 10^4 L\ cm^{-1}\ mol^{-1}$.

H-phosphonate RNA synthesis. The RNA synthesis was carried out on an extensively modified Biosearch 8750, essentially as described previously for DNA synthesis.[2] The exact coupling cycle used for RNA decmaer synthesized with allyl linker and RNA decamer synthesized with prior art succinate linker was:

1. Wash: $CH_2Cl_2$, 20 sec wash, 10 sec wait, repeated five times;
2. Deblock: 2.5% DCA/$CH_2Cl_2$, for purines: 20 sec acid, 10 sec wait, 40 sec acid; for pyrimidines: 20 sec acid, 20 sec wait, then 10 sec acid, 20 sec wait, repeat last two steps three times;
3. Wash: $CH_2Cl_2$, 50 sec;
4. Wash: pyridine/$CH_3CN$ (1:1 v/v), 20 sec wash, 10 sec wait, repeat five times;
5. Couple: 0.05 M H-phosphonate, 0.2 sec; 0.25 M AdCOCl, 0.2 sec, repeat nine to ninety nine times;
6. Wash: pyridine/$CH_3CN$, 20 sec wash, 10 sec wait, repeat four times;
7. Cap: 0.05 M cyanoethyl H-phosphonate, 0.2 sec; 0.25 M AdCOCl, 0.2 sec, repeat fifty nine times;
8. Wash: pyridine/$CH_3CN$, 20 sec wash, 10 sec wait, repeat four times;
9. Repeat: repeat from step 1 until desired sequence is complete;
10. Oxidize: 0.5 sec 0.4 M $I_2$ in THF, 0.5 sec pyridine/NMI/$H_2O$/THF (10/2/10/78), 30 sec wait, repeat 30 times; then 0.5 sec 0.4 M $I_2$ in THF, 0.5 sec TEA/$H_2O$/THF (10/10/80), 30 sec wait, repeat 30 times;
11. Wash: pyridine/$CH_3CN$, 20 sec wash, 10 sec wait, repeat 30 times.

Deprotection of RNA Decamer Synthesized with the Allyl Linker. The synthesis cartridge was connected between two disposable syringes, one of which contained 4 mL of a mixture of concentrated aqueous ammonia and 95% ethanol (3:1). Approximately 2 mL of this mixture was displaced through the cartridge and the sealed unit was maintained at room temperature for 16 h. The ammonia solution was then displaced, and the cartridge washed three times with about 10 mL of THF. The same double syringe apparatus then was charged with 4 mL of 1.0 M TBAF. After 4 h the TBAF solution was displaced and a fresh 4 mL portion of TBAF was added. After 16 h the TBAF was removed and the cartridge washed three times with about 10 mL of THF.

Cleavage of RNA Decamer Synthesized with the Allyl Linker from the PS/PEG Support. To the support-bound decamer synthesized with the allyl linker (35 μmole scale synthesis) was added 35 mg (0.03 mmol) of tetrakis (triphenylphosphine) palladium, 31 mg (0.12 mmol) of triphenylphosphine, and a 4 mL portion of n-butylammonium formate in pyridine and THF. This solution was prepared by adding 160 mg (3.5 mmol) of formic acid to 220 mg (3.5 mmol) of n-butylamine in 5 mL of THF, followed by addition of formic acid to produce a clear solution, and finally by addition of 1 mL of pyridine. The heterogeneous reaction mixture was sparged with nitrogen, sealed, and heated at 60° C. for 2 h. After cooling to room temperature, the mixture was centrifuged, the supernatant removed, and the solid washed twice with THF. The product was then eluted from the support with two 3 mL portions of 0.1 M TEAA buffer containing 1–3 mg of dimethyldithicarbamate.

Deprotection of RNA Decamer Synthesized by using Succinate Linker and Cleavage from the PS/PEG Support. The support was removed from the reaction cartridge and treated with concentrated aqueous ammonia and 95% ethanol (3:1) at room temperature for 16 h in a 50 mL centrifuge tube. The mixture was centrifuged, the supernatant removed, and the solid washed three times with water. The combined solutions were concentrated to remove most of the ammonia, and lyophilized. The residue was treated with 5 mL of 1.0 M TBAF in THF for 12 h, and the mixture concentrated to a gum.

Purification of RNA Decamer Synthesized Using Allyl Linker and Identical RNA Decamer Synthesized using Succinate Linker. The procedure for purification of RNA decamer synthesized using allyl linker and prior art succinate linker is nearly identical, except that the first HPLC purification of the RNA decamer synthesized using the succinate linker was done in two portions because of the large amount of TBAF. The first purification was carried out on a Waters C18 reversed-phase column (25×100 mm RCM cartridge) using a gradient of 2–40% acetonitrile: 0.1 M TEAA in 45 min at a flow rate of 4 mL/min. The appropriate fractions were combined, diluted with an equal volume of water and lyophilized. The residue was dissolved in water and an equal volume of 0.2 M acetic acid added to give a solution with a pH of about 3.2. The detritylation was complete after 20 min (HPLC). The pH was adjusted to 6 and the solution was lyophilized. The residue was dissolved in 0.1 M TEAA, filtered, and purified using a Beckman Ultrapore C3 column (10 mm×25 cm) using a gradient of 2–20% acetonitrile: 0.1 M TEAA in 45 min at a flow rate of 2 mL/min. The appropriate fractions were combined, diluted with an equal volume of water and lyophilized. The residue was dissolved in 0.1 M ammonium bicarbonate (ABC) and chromatographed on the C18 column using a gradient of 2–40% acetonitrile: 0.1 M ABC in 35 min at a flow rate of 4 mL/min. The appropriate fractions were combined, diluted with an equal volume of water and lyophilized. The residue was dissolved in water and applied to a Bio-Rad AG50W-X4 sodium-form ion-exchange column eluted with water. The appropriate fractions were combined and lyophilized to give RNA decamer synthesized using the allyl linker or RNA decamer synthesized using the succinate linker as the sodium salt.

Enzymatic Conversion of RNA Decamer Synthesized Using the Allyl Linker to RNA Oligomer Synthesized Using the Succinate Linker. To a 1.0 $OD_{260}$ sample of RNA synthesized using the allyl linker in 1 mL of 0.1 M TEAA was added 0.04 unit of calf intestinal phosphatase (CIP). Ion-exchange HPLC showed that the 3'-phosphate group was completely removed within 1 h, and that there was no further change after an additional 7 h.

Enzymatic Degradation of RNA Decamer Synthesized Using the Allyl Linker and Identical RNA Decamer Synthesized Using the Succinate Linker. To a 1 $OD_{260}$ sample of RNA decamer synthesized using the allyl linker or synthesized using the succinate linker in 1 mL of 0.1 M TEAA was added 1 unit of nuclease P1. After 1 h at room temperature, the pH was adjusted to 9–10 using 10% sodium carbonate and 1 unit of CIP was added. Degradation to ribonucleosides was complete within 1 h.

References for Example Section (all references incorporated herein in their entireties).

(1) Rapp Polymere, Tübingen, TentaGel Resin 30,002
(2) Gao, H.; Gaffney, B. L.; Jones, R. A. *Tetrahedron Lett.* 1991, 32, 5477–5480.

References for detailed disclosure (all references are incorporated herein in their entireties):

(1) Pon, R. T. in *Protocols for Oligonucleotides and Analogs*, Agrawal, S. ed.; Humana Press: Totowa, N.J., 1993; Vol. 20.
(2) Beaucage, S. L.; Iyer, R. P. *Tetrahedron* 1992, 48, 2223–2311.
(3) Sproat, B.; Colonna, F.; Mullah, B.; Tsou, D.; Andrus, A.; Hampel, A.; Vinayak, R. *Nucleosides & Nucleotides* 1995, 14, 255–273.
(4) Gaspaeutto, D.; Livache, T.; Bazin, H.; Duplaa, A.-M.; Guy, A.; Khorlin, A.; Molko, D.; Roget, A.; Téoule, R. *Nucleic Acids Res.* 1992, 20, 5159–5166.
(5) Westman, E.; Stromberg, R. *Nucleic Acids Res.* 1994, 22, 2430–2431.
(6) Hayakawa, Y.; Uchiyama, M.; Kato, H.; Noyori, R. *Tetrahedron Lett.* 1985, 26, 6505–6508.
(7) Hayakawa, Y.; Kato, H.; Uchiyama, M.; Kajino, H.; Noyori, R. *J. Org. Chem* 1986, 51,2400–2402.
(8) Hayakawa, Y.; Wakabayashi, S.; Kato, H.; Noyori, R. *J. Am. Chem. Soc.* 1990, 112, 1691–1696.
(9) Kunz, H.; Dombo, B. *Angew. Chem. Int. Ed Engl.* 1988, 27, 711–713.
(10) Blankemeyre-Menge, B.; Frank, R. *Tetrahedron Lett.* 1988, 46, 5871–5874.
(11) Guibé, F.; Dangles, O.; Balavoine, G. *Tetrahedron Lett.* 1989, 30, 2641–2644.
(12) Umbreit, M. A.; Sharpless, K. B. *J. Am. Chem. Soc.* 1977, 99, 5526–5528.
(13) The Aldrich price for 1 is $10.55 for 100 mL.
(14) Gao, H.; Gaffney, B. L.; Jones, R. A. *Tetrahedron Lett.* 1991, 32, 5477–5480.
(15) Gao, H.; Ph.D. Thesis, Rutgers, The State University of New Jersey, 1991.
(16) Horn, T.; Urdea, M. S. *Nucleic Acids Res.* 1988, 16, 11559–11571.
(17) Minczewski, J.; Chwastowska, J.; Dybczynski, R. *Separation and Preconcentration Methods in Inorganic Trace Analysis*; John Wiley & Sons: New York, 1982, pp 207–209.

What is claimed is:

1. An allylic linker comprising the following compound

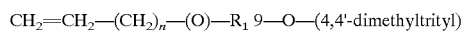

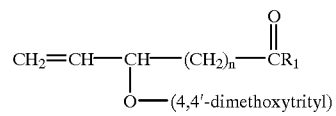

wherein $R_1$ is selected from the group consisting of OH, $OR_2$ and an amino functionalized support and n is an integer ranging from 0 to about 1000 and $R_2$ is an alkyl ($C_{1-20}$).

2. The compound of claim 1 wherein n is an integer ranging from 0 to about 100.

3. The compound of claim 1 wherein n in an integer ranging from 0 to about 12.

4. The compound of claim 1 that is 9-O-(4,4'-dimethoxytrityl)-10-undecenoic acid.

5. A method of preparing an allyl linker for solid phase synthesis comprising the steps of oxidizing a terminal alkenoic acid to produce the corresponding allylic alkoxy derivative and tritylating said allylic alkoxy derivative by reacting a 4,4'-dimethoxytrityl moiety with said allylic alkoxy derivative to produce a compound having the formula

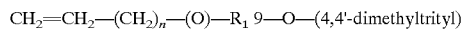

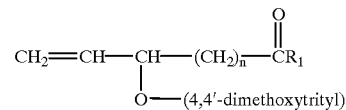

wherein $R_1$ is selected from the group consisting of OH, $OR_2$ and an amino functionalized support and n is an integer ranging from 0 to about 1000 and $R_2$ is an alkyl ($C_{1-20}$).

* * * * *